United States Patent [19]
Bacon et al.

[11] Patent Number: 5,322,679
[45] Date of Patent: Jun. 21, 1994

[54] IODINATED AROYLOXY ESTERS

[75] Inventors: Edward R. Bacon, Audubon, Pa.; Sol J. Daum, Albany; Paul P. Spara, Fairport, both of N.Y.

[73] Assignee: Sterling Winthrop Inc., New York, N.Y.

[21] Appl. No.: 990,987

[22] Filed: Dec. 16, 1992

[51] Int. Cl.$^5$ ............................................. A61K 49/04
[52] U.S. Cl. ............................................. 424/5; 560/47
[58] Field of Search ............................. 560/47; 424/5

[56]  References Cited
U.S. PATENT DOCUMENTS 3,144,479  8/1964  Herrmann et al. .................. 560/47
5,145,684  9/1992  Liversidge et al. ................ 424/489

FOREIGN PATENT DOCUMENTS 241516  6/1962  Australia .
866184  4/1961  United Kingdom .

OTHER PUBLICATIONS

Search Reports and CA:57:4603; 1962.
Myelographic Agents: J. Siggins et al. J. Med. Chem 8(5), 728-30 (1965) Chemical Abstracts CA63:14748e.

Primary Examiner—José G. Dees
Assistant Examiner—Samuel Barts
Attorney, Agent, or Firm—William J. Davis; Liza D. Hohenschutz

[57]  ABSTRACT

Compounds having the structure $$(Z)_{\hspace{-2pt}\text{\scriptsize{+}}}\!\!\overset{O}{\underset{\|}{C}}\!-\!O\!-\!\underset{\underset{R^2}{|}}{\overset{\overset{R^1}{|}}{C}}\!\!\left(\!\!\underset{\underset{R^4}{|}}{\overset{\overset{R^3}{|}}{C}}\!\!\right)_{\!\!\overline{n}}\overset{O}{\underset{\|}{C}}\!-\!O\!-\!R^5$$

wherein
  (Z)—COO is the residue of an iodinated aromatic acid;
  n is an integer from 1 to 20;
  $R^1$ and $R^2$ are independently H, alkyl, fluoroalkyl, cycloalkyl, aryl, aralkyl, alkoxy or aryloxy;
  $R^3$ and $R^4$ are independently H, alkyl, fluoroalkyl, cycloalkyl, aryl, aralkyl, alkoxy, aryloxy, halogen, hydroxy or acylamino; and
  $R^5$ is alkyl, cycloalkyl, aryl, aralkyl, alkoxyalkyl or acetamidoalkyl;
are useful as contrast agents in x-ray imaging compositions and methods.

7 Claims, No Drawings

IODINATED AROYLOXY ESTERS

FIELD OF INVENTION

This invention relates to iodinated aroyloxy esters which are particularly useful as contrast agents for x-ray

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on iodinated and other contrast agents for medical imaging is provided by D.P. Swanson et al, *Pharmaceuticals in Medical Imaging*, 1990, MacMillan Publishing Company.

The following references describe various iodine containing compounds useful in preparing x-ray contrast compositions.

U.S. Pat. No. 3,097,228 describes derivatives of 2,4,6-triiodobenzoyloxyalkanoic acids having the structure

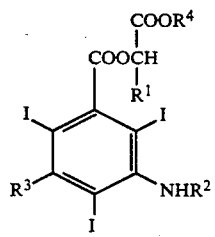

wherein $R^1$ is H or lower alkyl; $R^2$ is H or lower-alkanoyl; and $R^3$ is H or lower alkanoylamino and $R^4$ is lower alkyl.

U.S. Pat. No. 3,144,479 describes iodinated benzoic acid esters having the formula

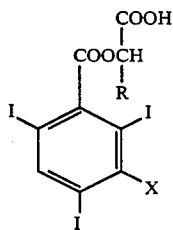

wherein X is an iodine atom or an amino group and R is selected from H, alkyl, alkoxyalkyl, i.e., $-(CH_2)_m-O-R''$, wherein R'' is alkyl and m is 1 or 2, phenyl and a particular iodinated aromatic group.

However, these references do not disclose or suggest compounds featuring an ester group linked through a $C_2$ or higher alkylene group to another ester group on an iodinated aromatic ring.

EP-A 498,482 describes nanoparticulate x-ray contrast compositions which have proven to be extremely useful in medical imaging. However, particulate contrast agents in certain in vivo applications can exhibit less than fully satisfactory solubility profiles and/or enzymatic degradation, e.g., in plasma and blood.

It would be desirable to provide compounds for use as x-ray contrast agents having improved enzymatic degradability and appropriate solubility profiles.

SUMMARY OF THE INVENTION

We have discovered and prepared novel iodinated aroyloxy esters which are useful as contrast agents in x-ray imaging compositions and methods.

More specifically, in accordance with this invention, there are provided compounds having the structure

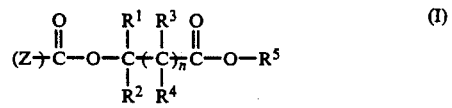

wherein
- $(Z)-COO$ is the residue of an iodinated aromatic acid;
- n is an integer from 1 to 20;
- $R^1$ and $R^2$ are independently H, alkyl, fluoroalkyl, cycloalkyl, aryl, aralkyl, alkoxy or aryloxy;
- $R^3$ and $R^4$ are independently H, alkyl, fluoroalkyl, cycloalkyl, aryl, aralkyl, alkoxy, aryloxy, halogen, hydroxy or acylamino; and
- $R^5$ is alkyl, cycloalkyl, aryl, aralkyl, alkoxyalkyl or acetamidoalkyl.

This invention further provides an x-ray contrast composition comprising the above-described compound and a method for medical x-ray diagnostic imaging which comprises administering to the body of a test subject an effective contrast producing amount of the above-described x-ray contrast composition.

It is an advantageous feature of this invention that novel compounds are provided which find particular utility as x-ray contrast agents.

It is another advantageous feature of this invention that compounds are provided having improved enzymatic degradability and appropriate solubility profiles.

DESCRIPTION OF PREFERRED EMBODIMENTS

In structural formula I above, $(Z)-COO$ is the residue of an iodinated acid. The iodinated aromatic acid can comprise one, two, three or more iodine atoms per molecule. Preferred species contain at least two, and more preferably, at least three iodine atoms per molecule. The iodinated compounds can contain substituents which do not deleteriously effect the contrast enhancing capability of the compound.

Illustrative examples of suitable aromatic acids include diatrizoic acid,
metrizoic acid,
urokonic acid,
iothalamic acid,
trimesic acid,
ioxaglic acid (hexabrix),
ioxitalamic acid,
tetraiodoterephthalic acid,
iodipamide, and the like.

In preferred embodiments, $(Z)-COO$ is the residue of a substituted triiodobenzoic acid such as an acyl, carbamyl, and/or acylamino substituted triiodobenzoic acid.

$R^1$ and $R^2$ independently represent H; linear or branched alkyl, preferably containing from 1 to 20, more preferably 1 to 8 carbon atoms such as methyl, ethyl, propyl, isopropyl, butyl, pentyl, hexyl and the like; fluoroalkyl, the alkyl portion of which is as described above and containing from 1 to (2m+1) fluorine atoms (where m=the number of carbon atoms in the alkyl group), such as trifluoromethyl; cycloalkyl, preferably containing from 3 to 8 carbon atoms such as cyclopropyl, cyclobutyl, cyclopentyl and cyclohexyl; aryl, preferably containing from 6 to 10 carbon atoms, such as phenyl and naphthyl; aralkyl, preferably containing from 7 to 12 carbon atoms, such as benzyl; alkoxy, the alkyl portion of which contains from 1 to 20 carbon atoms as described above; or aryloxy, the aryl portion of which preferably contains from 6 to 10 carbon atoms as described above.

$R^3$ and $R^4$ independently represent a substituent as defined for $R^1$ above; halogen, such as chlorine, bromine or iodine; hydroxy; or acylamino, i.e., a

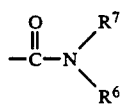

group wherein $R^6$ and $R^7$ are independently H, alkyl, aryl, aralkyl or alkoxy as defined for $R^1$ above, acetamidoalkyl, i.e.,

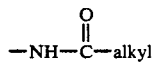

wherein alkyl is as defined for $R^1$ above, —COO—alkyl, the alkyl portion of which is as defined for $R^1$ above, cyano and the like, or $R^6$ and $R^7$, taken together with the nitrogen atom to which they are attached, represent a 4–7 membered saturated or unsaturated nitrogen containing ring such as piperidyl, piperizinyl, pyrrolidinyl, and the like. However, reactive substituents such as halogen, hydroxy, and acylamino are not preferred on carbon atoms adjacent to the ester groups.

$R^5$ represents alkyl as defined for $R^1$ above; cycloalkyl as defined for $R^1$ above; aryl as defined for $R^1$ above, aralkyl as defined for $R^1$ above; alkoxy, as defined for $R^1$ above; aryloxy, as defined for $R^1$ above; alkoxyalkyl, the alkyl and alkoxy portions of which are as defined for $R^1$ above; or acetamidoalkyl; i.e.,

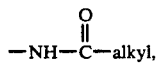

wherein alkyl is as defined for $R^1$ above.

The alkyl, cycloalkyl, aryl, aralkyl and alkoxy groups in structure I above can be unsubstituted or substituted with various substituents which do not adversely affect the stability or efficacy of the compounds as x-ray contrast agents such as alkyl, cycloalkyl, aryl, aralkyl, alkoxy, hydroxy, acyloxy, halogen, such as chlorine, bromine and iodine, acylamino, carboalkoxy, carbamyl and the like. However, reactive substituents such as halogen are not preferred on the carbon atoms, if present in $R^5$ adjacent to the ester group.

The compounds of this invention can be prepared by contacting the carboxylate of an iodinated aromatic acid with a functionalized ester having the formula

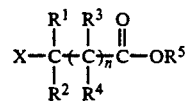

wherein X is a leaving group and n and $R^1$-$R^5$ are as defined above, in a suitable solvent. Suitable leaving groups include halogen, such as Br, I and Cl, sulfonyloxy, such as methanesulfonyloxy and toluenesulfonyloxy. Suitable solvents include dimethylformamide. The carboxylates of iodinated aromatic acids and functionalized esters useful as the starting materials in the preparation of the compounds of this invention are known compounds and/or can be prepared by techniques known in the art. For example, suitable esters include commercially available bromoesters and chloroesters derivatives as exemplified below. A general reaction scheme is as follows:

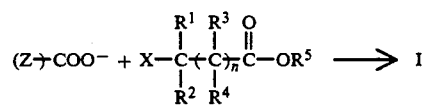

The reaction can take place at various temperatures ranging between −78° C. and 100° C., and preferably −40° C. and 50° C. For convenience, the reaction can take place at ambient pressure, however, higher and lower pressures are contemplated.

Preferred compounds of this invention conform to structure I above, wherein $R^1$-$R^4$=H as indicated below:

| WIN | Z | n | $R^5$ |
|---|---|---|---|
| 67722 | ![structure with CH3CONH, I, NHCOCH3] | 4 | $C_2H_5$ |
| 67954 | " | 3 | $C_2H_5$ |
| 67995 | " | 4 | $CH(CH_3)_2$ |
| 68039 | " | 4 | $CH_2OCOC(CH_3)_3$ |
| 68061 | " | 2 | $C_2H_5$ |
| 68060 | " | 2 | $CH_2$—$C_6H_5$ |
| 68136 | " | 5 | $C_2H_5$ |
| 68166 | " | 6 | $C_2H_5$ |
| 68767 | ![structure with CH3COHN, I, NCOCH3, CH3] | 4 | $C_2H_5$ |
| 68888 | " | 3 | $C_2H_5$ |
| 68384 | ![structure with I, NHCOCH3] | 4 | $C_2H_5$ |
| 68038 | ![structure with (CH3CO)2N, I, N(COCH3)2] | 4 | $C_2H_5$ |

| WIN | Z | n | R⁵ |
|---|---|---|---|
| 69732 | C₂H₅CO₂(CH₂)₅ — [triiodobenzene ring with I, I, I and NHCOCH₃] | 4 | C₂H₅ |

When used as an x-ray contrast agent, the compound of this invention preferably comprises at least about 35%, more preferably 40% iodine by weight.

In preferred embodiments, the compounds of this invention can be formulated into particulate x-ray contrast compositions, preferably nanoparticulate x-ray contrast compositions, as described in commonly-owned EPO 498,482, the disclosure of which is hereby incorporated by reference in its entirety. Such nanoparticulate compositions can be prepared by dispersing the compounds of the invention in a liquid dispersion medium, and wet grinding the compound in the presence of rigid grinding media and a surface modifier to form the nanoparticles. Alternatively, the surface modifier can be contacted with the compound after attrition.

The x-ray contrast compositions of this invention comprise the above-described compounds, preferably in the form of particles, and a physiologically acceptable carrier therefor. For example, the particles can be dispersed in an aqueous liquid which serves as the carrier for the x-ray contrast agent. Other suitable carriers include liquid carriers such as mixed aqueous and nonaqueous solvents, such as alcohol; gels; gases, such as air; and powders.

The x-ray contrast composition can comprise from about 1–99.9, preferably 2–45 and more preferably 10–25% by weight of the above-described particles, the remainder of the composition being the carrier, additives and the like. Compositions up to about 100% by weight of the particles are contemplated when the composition is in a lyophilized form.

The dose of the contrast agent to be administered can be selected according to techniques known to those skilled in the art such that a sufficient contrast enhancing effect is obtained. Typical doses can range from 50 to 350 mg of iodine per kilogram of body weight of the subject for many imaging applications. For some applications, e.g., lymphography, lower doses, e.g., 0.5–20 mg I/kg, can be effective.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a convention manner. Alternatively, the image pattern can be observed directly on an x-ray sensitive phosphor screen-silver halide photographic film combination.

The compositions of this invention can be administered by a variety of routes depending on the type of procedure and the anatomical orientation of this tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like.

In addition to preferred applications, i.e., for blood pool, liver, spleen and lymph node imaging, the x-ray contrast compositions of this invention are also expected to be useful as contrast agents for any organ or body cavity. For example, the compositions of this invention are expected to be useful as angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The following examples further illustrate the invention.

EXAMPLE 1

Synthesis of WIN 67722 (6-Ethoxy-6-oxohexyl 3.5-bis(acetylamino)-2,4,6-triiodobenzoate)

Sodium diatrizoate (16.1 g, 25.3 mmol) was dissolved in 180 ml of dry dimethylformamide and to this solution was added, in one portion, ethyl 6-bromohexanoate (4.5 ml, 25.3 mmol). The reaction mixture was stirred for 12 hr at ambient temperature and then poured into 1.6 l of ice-water with stirring. The resulting white precipitate was collected by filtration, dissolved in 1:1 ethanol-ethyl acetate and the solution was treated with magnesium sulfate, decolorizing charcoal and then filtered through a short pad of silica gel. The filtrate was concentrated to dryness and dried to give 16 g (84%) of the desired product. Recrystallization from methanol water gave analytically pure material, mp 235°–238° C. (decomp. at 275° C.); MS:M+756. The ¹H-NMR (300 MHz) spectral data was consistent with the desired product. Calculated for $C_{19}H_{23}I_3N_2O_6$: C 30.18, H 3.07, I 50.35, N 3.70; Found: C 30.26, H 2.88, I 50.40, N 3.65.

EXAMPLE 2

Synthesis of WIN 67954 (5-Ethoxy-5-oxopentyl 3,5-bis(acethylamino)-2,4,6-triiodobenzoate To a stirred solution of sodium diatrizoate (59.0 g, 92.8 mmol) in 350 ml of dry DMF was added ethyl 5-bromovalerate (14.7 ml, 92.8 mmol) in two portions and the resulting solution was stirred at ambient temperature for 12 hr. The reaction mixture was poured into 3.5 l of water and the resulting white precipitate was collected, washed with ether and then air dried. The crude product was dissolved in acetonitrile-ethanol (5:2), filtered through a pad of silica gel and the filtrate was evaporated to give a solid (67 g, 97%). Recrystallization from methanol-water gave analytically pure product (mp 237°-239° C) after drying under high vacuum; CI-MS: MH+743. The $^1$H-NMR (300 MH$_z$) spectral data was consistent with the desired product. Calculated for $C_{18}H_{21}I_3N_2O_6$; C 29.13, H 2.85, I 51.30; Found: C 29.13, H 2.78, I 51.15, N 3.75.

EXAMPLES 3-13

In a manner similar to the procedures described in Examples 1 and 2 above, the compounds set forth in the Table above were prepared. In each case, the MS and spectral data (300 MH$_z$) were consistent with the desired product.

The invention has been described in detail with particular reference to certain preferred embodiments thereof, but it will be understood that variations and modifications can be effected within the spirit and scope of the invention.

We claim:

1. A compound having the structure:

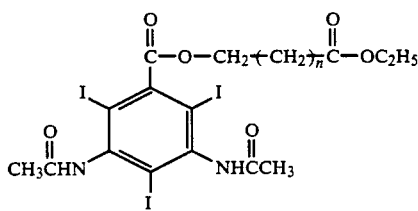

wherein n is 3, 4, 5 or 6.

2. The compound of claim 1 having the structure:

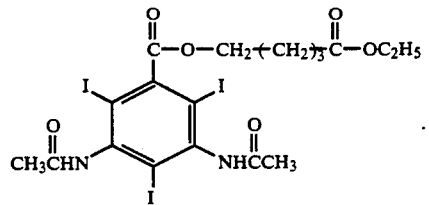

3. The compound of claim 1 having the structure:

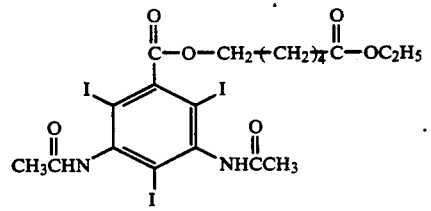

4. The compound of claim 1 having the structure:

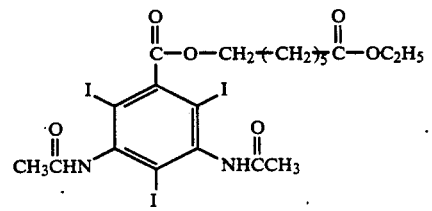

5. The compound of claim 1 having the structure:

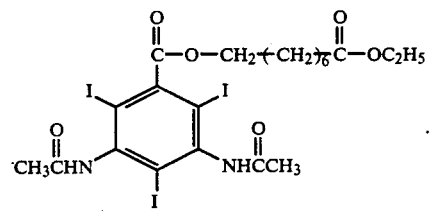

6. An x-ray contrast composition comprising the compound of claim 1.

7. The x-ray contrast composition of claim 6 further including a pharmaceutically acceptable carrier.

* * * * *